(12) United States Patent
Yang

(10) Patent No.: US 8,535,704 B2
(45) Date of Patent: Sep. 17, 2013

(54) SELF-ASSEMBLING CROSS-LINKING MOLECULAR NANO FILM

(75) Inventor: Zhongping Yang, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 1928 days.

(21) Appl. No.: 11/322,055

(22) Filed: Dec. 29, 2005

(65) Prior Publication Data

US 2007/0154519 A1    Jul. 5, 2007

(51) Int. Cl.
*A61F 2/02*      (2006.01)
(52) U.S. Cl.
USPC .......................................... 424/424; 977/931
(58) Field of Classification Search
None
See application file for complete search history.

(56) References Cited

U.S. PATENT DOCUMENTS

| | | |
|---|---|---|
| 4,011,861 A | 3/1977 | Enger |
| 4,573,480 A | 3/1986 | Hirschberg |
| 5,061,738 A | 10/1991 | Solomon |
| 5,090,422 A | 2/1992 | Dahl et al. |
| 5,148,806 A | 9/1992 | Fukui et al. |
| 5,269,810 A | 12/1993 | Hull et al. |
| 5,358,516 A | 10/1994 | Myers et al. |
| 5,466,252 A | 11/1995 | Soukup et al. |
| 5,609,622 A | 3/1997 | Soukup et al. |
| 5,755,762 A | 5/1998 | Bush |
| 6,119,028 A | 9/2000 | Schulman |
| 6,372,283 B1 | 4/2002 | Shim |
| 2003/0204230 A1 | 10/2003 | Yang |
| 2005/0038219 A1 | 2/2005 | Lai |
| 2005/0219788 A1 * | 10/2005 | Chow et al. .................. 361/305 |

FOREIGN PATENT DOCUMENTS

| | | |
|---|---|---|
| EP | 0608921 A | 8/1994 |
| WO | 97/18904 A | 5/1997 |
| WO | 01/34695 A | 5/2001 |
| WO | WO02089909 A1 | 11/2002 |
| WO | 2006/121573 A | 11/2006 |
| WO | 2007/056561 A | 5/2007 |

OTHER PUBLICATIONS

Lee et al. Protein-resistant coatings for glass and metal oxide surfaces derived from oligo(ethylene oxide)-terminated alkyltrichlorosilanes, Biomaterials 19 (1998) pp. 1669-1675.*
Zhang et al. Protein and cells on PEG immobilized silicon surfaces, Biomaterials 19 (1998) pp. 953-960.*

* cited by examiner

*Primary Examiner* — Shanon A Foley

(57) ABSTRACT

The present invention is a molecular nano film formed on a surface of an implantable medical device to provide a barrier to tissue attachment. The film comprises self-assembling cross-linking molecules.

10 Claims, 4 Drawing Sheets

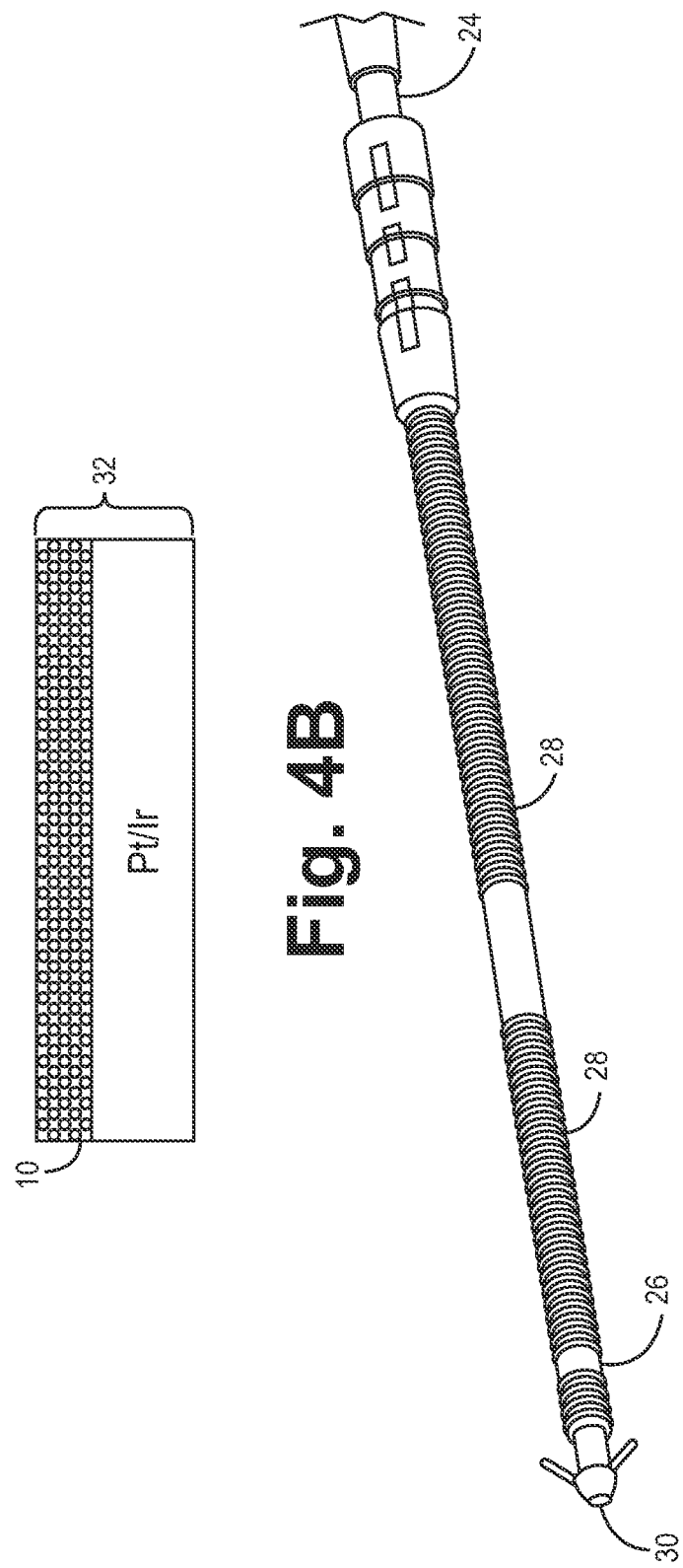

SELF-ASSEMBLING CROSS-LINKING MOLECULAR NANO FILM

BACKGROUND OF THE INVENTION

The present invention relates to the field of implantable medical devices and more particularly to chronically implantable medical devices provided with a porous, self-assembling, cross-linking mono or multi-molecular film.

It has become common to provide therapy and treat diseases using implantable medical devices (IMD) that are chronically implanted within the body of a patient. Examples of such medical devices include pacemakers, defibrillators, drug-delivery devices, and electro-stimulators for stimulating nerves, muscles, and other tissue.

One problem associated with the chronic implantation of IMDs involves the growth of fibrous tissue around the device. When a foreign object such as an IMD is introduced into a patient's body, the body's auto-immune system forms a collagen capsule around the foreign object. This capsule, which has fibrous tissue, attaches to the IMD in a manner that prevents easy extraction of the device. This makes it difficult to replace or re-locate a medical device after it has been in the body for any significant amount of time. This problem is particularly prevalent when dealing with implantable medical leads.

Implantable medical leads have many uses. For example, leads carrying electrodes and other sensors are often positioned within a chamber of the heart or in the associated vasculature. These leads may be used to deliver electrical stimulation to cardiac tissue, and/or to sense and detect physiological signals. Leads may also be utilized to deliver medication to the body as controlled by a drug delivery device. Leads may also release biologic agents or carry diagnostic and monitoring tools into a tissue or an organ.

As noted above, the formation of fibrous tissue surrounding an implantable medical lead results in problems when the lead is to be replaced or re-located. The problems are exacerbated by the formation of small micro cracks in the surface of the electrode body. These cracks result when leukocytes release oxygen-free radicals causing an autoxidation reaction at the electrode's surface. The small crevices create additional surface area and spaces within which fibrous tissue can bond, making chronic lead extraction even more difficult.

Many methods have been devised in attempts to prevent the bonding of collagenous capsule tissue to the surface of IMDs. If such bonding could be prevented, the extraction of chronically-implanted devices would be greatly simplified. One manner of attempting to prevent tissue in-growth describes coating a lead with a porous polytetrafluoroethylene (PTFE) layer having a pore size of less than 10 microns or smaller so that tissue in-growth is prevented.

Other methods of preventing tissue in-growth are directed more specifically at eliminating the formation of tissue around the electrode structures carried on some lead bodies. One technique involves injecting silicone rubber into the spaces between the individual coils of an electrode structure. The resulting thin coating of silicone rubber surrounding the exterior of the electrode coils minimizes tissue in-growth between the filars of the coils, while leaving a portion of the coils exposed to deliver electrical stimulation to a patient.

Although the foregoing mechanisms have been developed in attempt to prevent collagen formation with the surface of an IMD, problems still remain. Therefore, what is needed is an improved device and method to prevent tissue in-growth on the surface of a chronically-implanted medical device.

BRIEF SUMMARY OF THE INVENTION

A molecular nano film formed on a surface of an implantable medical device provides a barrier to tissue attachment. The film comprises self-assembling cross-linking molecules.

BRIEF DESCRIPTION OF THE DRAWINGS

FIG. 4A is a side view of a lead containing various electrodes incorporating the molecular nano film barrier.

FIG. 4B illustrates the molecular nano film on an electrode surface.

DETAILED DESCRIPTION

Coating a surface of an implantable medical device (IMD) with a molecular nano film protects the surface of the IMD in several ways. First, the molecular film operates to separate leukocytes from the IMD's surface. Leukocytes are structures within the body that release oxygen-free radicals when a foreign object is introduced into the body. These radicals react with the surface of an IMD causing autoxidation and formation of micro cracks. When surface cracking is prevented, it is more difficult for tissue to adhere to the surface of the IMD.

Second, the adhesion, proliferation and detachment of fibroblasts are decreased by the molecular film. The host's inflammatory response to an implant can lead to fibrous encapsulation. Increased fibroblast adhesion and proliferation causes an increase in collagen surrounding the implant that ultimately causes encapsulation. An IMD protected by a molecular film can be removed from encapsulated tissue with relatively little difficulty. Even a monolayer of the molecular nano film will operate in this manner. Some tissue attachment, however, does occur but to an extent that does not excessively interfere with removability.

Figure 1:
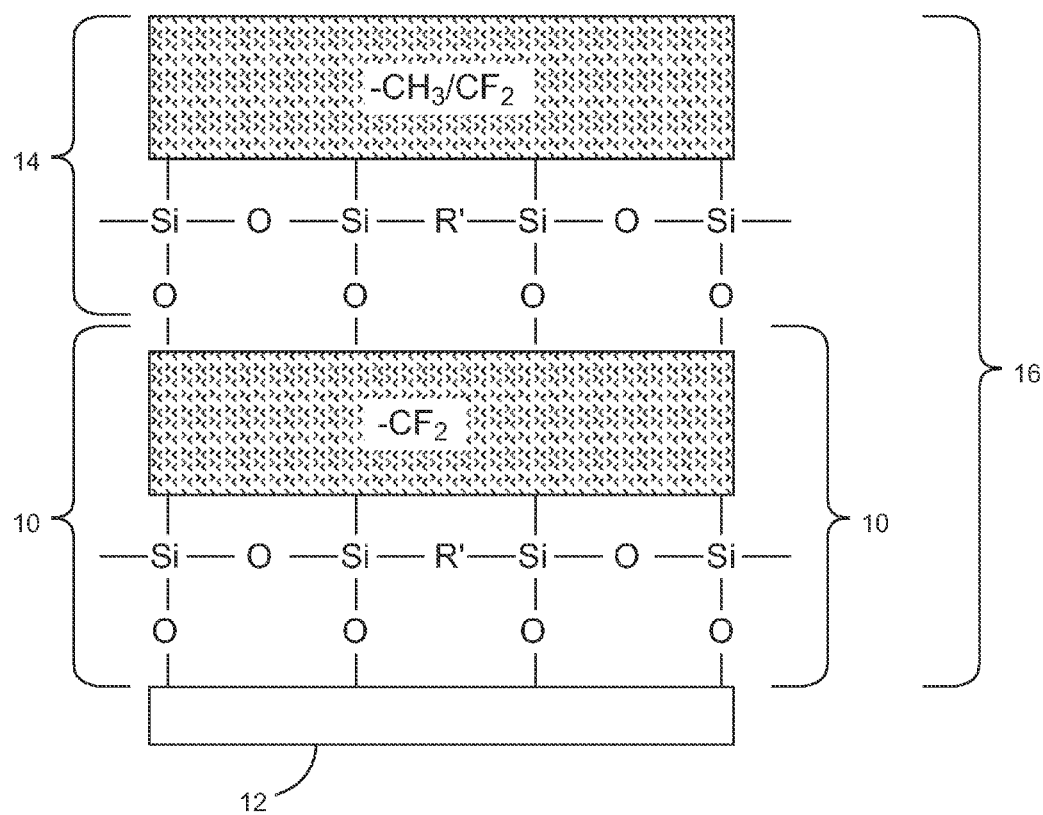
FIG. 1 is a schematic representation of a molecular nano film according to one embodiment of the present invention.

FIG. 1 is a schematic representation of self-assembling cross-linking molecular nano film 10 on a surface 12 of an IMD. Film 10 provides a thin, porous, conductive molecular film covering for surface 12. In one embodiment, film 10 is applied only to portions of surface 12. In other embodiments, the entirety of surface 12 is surrounded by film 10.

In FIG. 1, film 10 is illustrated in monolayer form. In other embodiments, several successive monolayer films (e.g. film 10, film 14 and so on) can be deposited, thereby creating a multilayer molecular nano film 16. Film 10 has a thickness in a range of about 2 to about 10 nanometers, with a pore size of about 0.2 to about 500 nanometers, and tightly conforms to the external profile of whatever surface it is covering, thereby minimizing air gaps and voids. The minimal air gaps, tight conforming nature, and porosity allows for repeated high energy discharges to be transmitted through the thin molecular film without dielectric breakdown or sparking.

Film 10 has pore sizes tailored to inhibit cellular ingrowth and encapsulation. The molecular film is porous, thereby allowing moisture, for example body fluids, within the pores in order to aid in electrical discharge associated with certain IMD's. Film 10 is continuous and tightly conforming to any portion of surface 12 to which it is exposed. The tightly conforming aspect of film 10 is a result of the application process used to apply film 10 onto surface 12. Film 10 can be hydrophobic and/or hydrophillic. In one embodiment, film 10 is non-conductive in a dry state (for example outside the body) and ionic conductive in a wet state (for example inside the body or when a sufficient amount of moisture or liquid is applied to film 10.)

Figure 2:
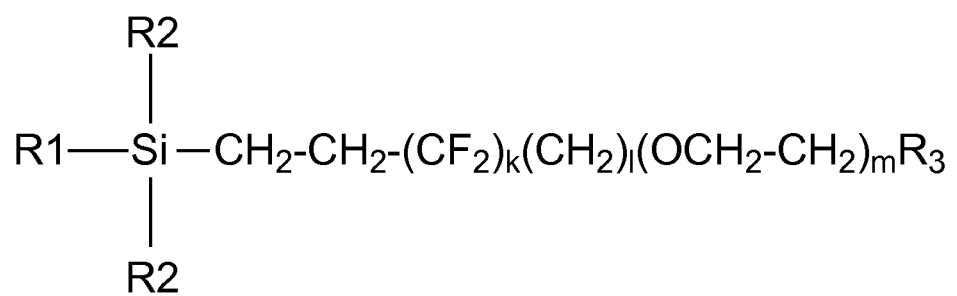
FIG. 2 is a schematic representation of a single molecule of the molecular nano film.

FIG. 2 is a schematic representation of a single molecule of film 10. The base group is a functional silane molecule. The functional silane molecule has four binding/bonding sites. In FIG. 2, R1 denotes halide-based (for example chlorine) or ether-based (for example ethylene oxide) attachment. R2 denotes halide-based, ether-based, or alkyl-based attachment. R3 denotes ether-based, ester-based (for example acetate), or carbonate (for example t-butyl carbonate) attachment. The letters "k," "l," and "m" each represent a range of about zero to about twenty.

In one embodiment, film 10 is made from fluorocarbon alkyltrichlorosilane. Fluorocarbon alkyltrichlorosilane is a non-reactive surface barrier, forcing the free radicals to react with something other than the film, thereby protecting surface 12 of the IMD. In other embodiments, film 10 and film 14 can be made from any element containing a functional silane molecule, for example fluorocarbon-alkyltrichlorosilane, hydrocarbon-alkyltrichlorosilane, ethylene oxide-alkyltrichlorosilane, a halide-alkylsilane, alkylsilane, an ethylene oxide-halidealkylsilane, and combinations thereof. In one embodiment, film 10 and film 14 are similar functional silane based films. In other embodiments, film 10 and film 14 are different functional silane based films.

Figure 3:
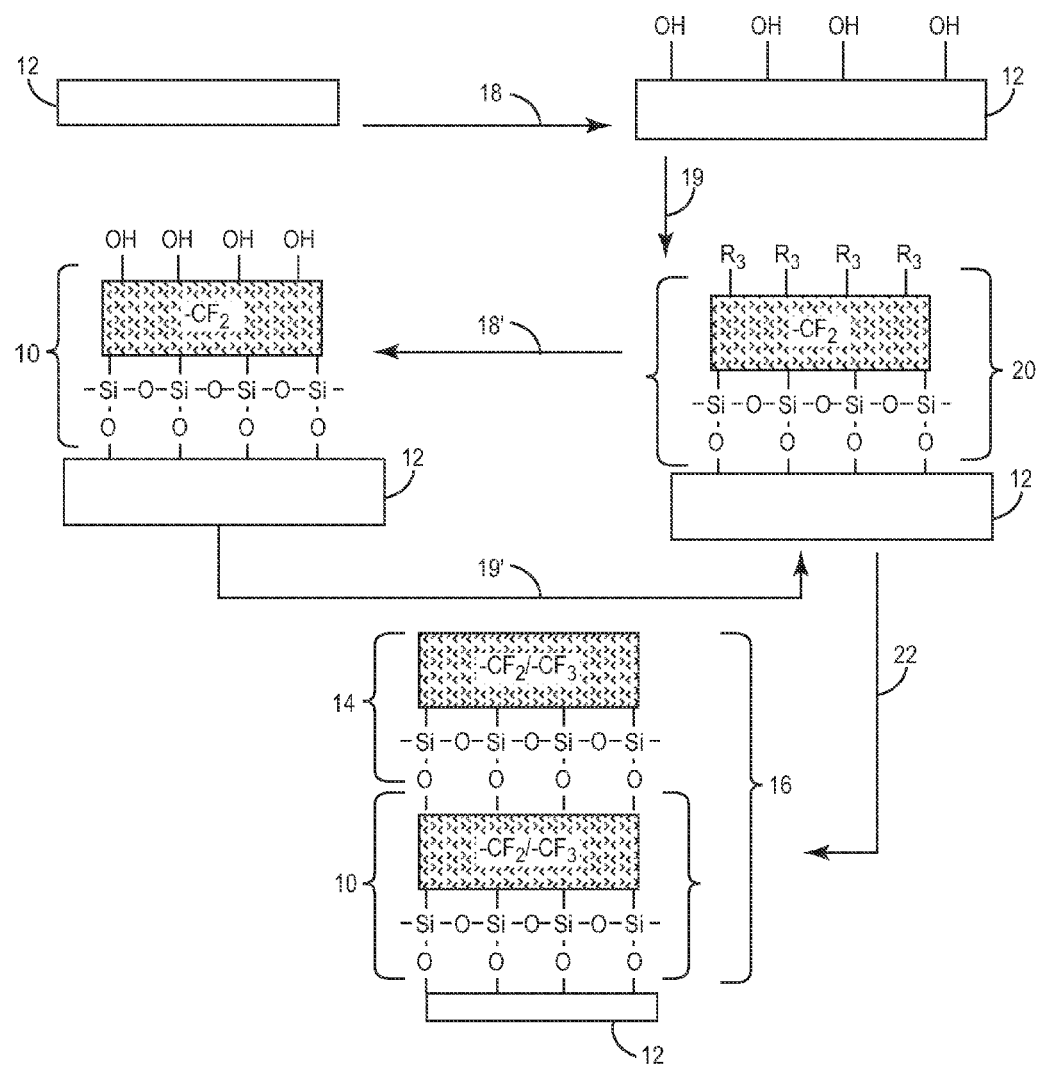
FIG. 3 is a diagram illustrating a method of forming the molecular nano film.

FIG. 3 is a diagram illustrating a method of forming molecular nano films 10 and 14 (thereby creating multilayer film 16) onto surface 12. The molecular nano film of the present invention is a self-assembling cross-linking film that is applied to surface 12 through molecular layer deposition, chemical vapor deposition, solution immersion, and combinations thereof. Molecular layer and chemical vapor deposition occur through an atomization process of the functional silane, whereas solution immersion allows surface 12 to be fully or partially immersed into a liquified solution containing the functional silane.

First, the portions of surface 12 that are to be coated with the molecular nano film are hydroxylated 18. Next, surface 12 with the attached OH groups are exposed to functional silane molecules through molecular layer deposition, chemical vapor deposition, solution immersion, or combinations thereof (all of which are represented by arrow 19). FIG. 3 illustrates fluorocarbon-alkyltrichlorosilane. In other embodiments, other functional silane molecules can be used. At this point, a monolayer film 20 with a terminal end group R3 is attached to surface 12. If only a monolayer film coating is desired, the deposition process would stop here.

If a multilayer film is desired, then film 20 is hydroxylated 18' in order to convert the attached R3 group to an OH group. Next, film 10 with the attached OH groups is exposed to functional silane molecules through molecular layer deposition, chemical vapor deposition, solution immersion, or combinations thereof (all of which are represented by arrow 19'). At this point, film 14 has been added to film 10. Arrow 22 represents either another hydroxylation step or termination of the process. FIG. 3 illustrates no further hydroxylation steps, and therefore arrow 22 signifies termination of the process thereby creating multilayer film 16 onto surface 12. In other embodiments, arrow 22 will signify continuation of the process and therefore the addition of subsequent layers of film.

Whichever type of functional silane molecule is used, it will be self-assembling and cross-linking, meaning that a single functional silane, for example fluorocarbon-alkyltrichlorosilane, will automatically attach itself to an exposed OH group on surface 12 and then subsequently cross-link to two adjacent fluorocarbon-alkyltrichlorosilane molecules that are bonded to two adjacent OH groups. This allows the film to be self-assembling (thereby allowing for faster film deposition) and cross-linking (providing a stronger film). The same process occurs if a multilayer film is created, once the R3 group of the initial functional silane molecule is hydroxylated.

FIG. 4A is a side view of a composite implantable defibrillator lead 24 containing three different types of electrodes. In other embodiments, other IMDs may be used, including surfaces of catheters, various leads, pacemakers, defibrillators, drug-delivery devices, electro-stimulators for stimulating nerves, muscles, or any other type of implantable device.

Lead 24 has three different electrode embodiments: ring electrode 26, helically wound electrode 28, and tip electrode 30. In one embodiment, portions of ring electrode 26, helically wound electrode 28, and tip electrode 30 are exposed to body tissue and fluids in order to deliver an electrical pulse or to sense electrical activity. These electrodes are typically fabricated from a non-corrosive, bio-compatible metal such as platinum, titanium and/or alloys such as platinum/iridium. In one embodiment of the present invention, the electrodes are comprised of about ninety percent platinum and about ten percent iridium.

In FIG. 4B, element 32 schematically illustrates molecular nano film 10 of the present invention, providing a barrier to tissue attachment, on the platinum/iridium surface of ring electrode 26, helically wound electrode 28, and tip electrode 30 of lead 24. In other embodiments lead 24 itself, or any other type of IMD, can be covered by nano film 10.

Although the present invention has been described with reference to preferred embodiments, workers skilled in the art will recognize that changes may be made in form and detail without departing from the spirit and scope of the invention.

The invention claimed is:

1. An implantable medical device, comprising an external surface of platinum, titanium or platinum/iridium and a self-assembling, cross-linking molecular nano film that is applied over an area of the external surface to inhibit tissue attachment to the external surface, the film comprising interactive molecule chains of a fluorocarbon-alkyltrichlorosilane that create pores permitting ionic conductivity between the external surface and surrounding biological material.

2. The implantable medical device of claim 1, wherein the film comprises a monolayer.

3. The implantable medical device of claim 2, wherein the monolayer has a thickness in a range of about 2 nanometers to about 10 nanometers.

4. The implantable medical device of claim 2, wherein the film comprises a plurality of monolayers, thereby creating a multilayer film structure.

5. The implantable medical device of claim 1, wherein the film comprises pores with a pore size in a range of about 0.2 nanometers to about 500 nanometers.

6. The implantable medical device of claim 1, wherein the film comprises functional silane molecules deposited through at least one of molecular layer deposition, chemical vapor deposition, solution immersion, and combinations thereof.

7. A method of providing a conductive barrier to tissue attachment on an implantable medical device, the method comprising:

hydroxylating at least one platinum, titanium or platinum/iridium surface of the device; and binding functional fluorocarbon-alkyltrichlorosilane molecules to the hydroxylated surface of the device, thereby forming a self-assembling cross-linking monolayer nano film.

8. The method of claim 7, wherein binding the functional silane molecules includes at least one of molecular layer deposition, chemical vapor deposition, solution immersion, and combinations thereof.

9. The method of claim 7, wherein each monolayer of the film has a thickness in a range of about 2 nanometers to about 10 nanometers.

10. The method of claim 7, wherein the film comprises a plurality of monolayers, thereby creating a multilayer film structure.

* * * * *